(12) United States Patent
Wang et al.

(10) Patent No.: US 11,976,038 B1
(45) Date of Patent: May 7, 2024

(54) PREPARATION METHOD OF RESVERATROL NERVONIC ACID ESTER

(71) Applicant: INSTITUTE OF FOOD SCIENCE AND TECHNOLOGY, CHINESE ACADEMY OF AGRICULTURAL SCIENCES, Beijing (CN)

(72) Inventors: Qiang Wang, Beijing (CN); Qin Guo, Beijing (CN); Tian Li, Beijing (CN); Xiaoning Hu, Beijing (CN); Manzhu Liang, Beijing (CN); Yang Qu, Beijing (CN); Zhenyuan Li, Beijing (CN)

(73) Assignee: INSTITUTE OF FOOD SCIENCE AND TECHNOLOGY, CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 18/399,457

(22) Filed: Dec. 28, 2023

(30) Foreign Application Priority Data

Mar. 24, 2023 (CN) .......................... 202310299194.9

(51) Int. Cl.
C07C 67/62 (2006.01)
C07C 37/82 (2006.01)
C07C 37/88 (2006.01)
C07C 67/56 (2006.01)

(52) U.S. Cl.
CPC .............. *C07C 67/62* (2013.01); *C07C 37/82* (2013.01); *C07C 37/88* (2013.01); *C07C 67/56* (2013.01)

(58) Field of Classification Search
CPC ......... C07C 67/62; C07C 37/82; C07C 37/88; C07C 67/56; C07C 67/08; C11B 5/0035
See application file for complete search history.

(56) References Cited

U.S. PATENT DOCUMENTS

2008/0004342 A1* 1/2008 Zaloga .................. C07H 17/06
514/506

FOREIGN PATENT DOCUMENTS

CN 107445826 12/2017
CN 112979464 6/2021

OTHER PUBLICATIONS

Shramko et al. (The Short Overview on the Relevance of Fatty Acids for Human Cardiovascular Disorders, Biomolecules, 10, 1127, p. 20, Published 2020) (Year: 2020).*
Linfang Zhou et al., "Synthesis of Polyunsaturated Fatty Acid Esters of Resveratrol", Journal of Food Science and Biotechnology, with English abstract, Jan. 15, 2020, pp. 31-37.
Office Action of China Counterpart Application, with English translation thereof, issued on Sep. 4, 2023, pp. 1-10.

* cited by examiner

*Primary Examiner* — Yevgeny Valenrod
*Assistant Examiner* — Blaine G Doletski
(74) *Attorney, Agent, or Firm* — JCIPRNET

(57) ABSTRACT

The present disclosure provides a preparation method of resveratrol nervonic acid ester, comprising the following steps of: step 1: weighing resveratrol, a nervonic acid and thiocarbonyldiimidazole according to a molar ratio of 1:1:0.8 to 1:7:11.2 in a reactor; step 2: adding a certain amount of solvent into the reactor to completely dissolve the reactants; and step 3: stirring for reaction at room temperature for 30 min to 180 min. The preparation method is safe, efficient and clean, and enables synthesis of the resveratrol nervonic acid ester with high conversion rate, high purity and high yield.

7 Claims, 3 Drawing Sheets

PREPARATION METHOD OF RESVERATROL NERVONIC ACID ESTER

CROSS-REFERENCE TO RELATED APPLICATION

This application claims the priority benefit of China application serial no. 202310299194.9, filed on Mar. 24, 2023. The entirety of the above-mentioned patent application is hereby incorporated by reference herein and made a part of this specification.

BACKGROUND

Technical Field

The present disclosure relates to the technical field of esterification modification for resveratrol. More specifically, the present disclosure relates to a preparation method of resveratrol nervonic acid ester.

Description of Related Art

Nervonic acid (C24: 1-15c) is an omega-9 very long-chain monounsaturated fatty acid, which has the functions of promoting brain health, enhancing immunity, lowering blood sugar, decreasing blood lipids, etc., and is the only new food ingredient discovered so far that can promote the repair and regeneration of damaged nerve tissue.

Resveratrol (3, 4', 5-trihydroxystilbene) is a natural polyphenol compound, which is abundant in plants such as peanuts, grapes and mulberries. Existing studies have reported that resveratrol has antitumor, anti-inflammatory, antibacterial, cardioprotective, neuroprotective, antioxidant, anti-isomeric and other effects. Currently, resveratrol is often used in dietary supplements, cosmetics, food and beverages, and has a huge market potential. However, due to its low solubility in water (30 mg/L) and oil (0.98 µg/g), and extremely low oral bioavailability (<1%), its application in food, medicine, cosmetics, etc. is greatly limited.

In order to further improve the lipid solubility of resveratrol, esterification modification and embedding methods are mostly used in current research. In the chemical embedding method, the resveratrol is loaded and encapsulated by using a single or multiple materials such as polysaccharides, proteins and polyphenols, which have the characteristics of continuous release; but these materials are susceptible to phase separation due to non-covalent bonding, and the stability of the embedding system is reduced due to the aggregation of emulsions (temperature or pH change). However, the esterification modification is simpler and more economical as hydrophilic or lipophilic groups can be introduced into its existing structure through the action of catalysts or enzymes. Among these methods, due to the low conversion rate and yield of enzymatic esterification, chemical esterification is mostly used.

At present, aromatic acids, short chain fatty acids (C3-C5), medium chain fatty acids (C6-C12), and long chain fatty acids (C13-C21) are mostly used in studies to improve the lipid solubility of resveratrol. Very long chain fatty acids (C22-C30), which have the advantages of high melting point, low calorific value and high stability, can improve the crystallization properties of plastic fats and synthesize low-calorie foods. Due to the difficulty of chain length synthesis, and the extremely low esterification rate, purity and yield (10.2%) of existing studies, it is urgent to establish a fast and efficient method for synthesizing very long chain fatty acid esters.

SUMMARY

It is an object of the present disclosure to provide a preparation method of resveratrol nervonic acid ester, which is safe, efficient and clean, and enables synthesis of the resveratrol nervonic acid ester with high conversion rate, high purity and high yield.

In order to achieve these objects and other advantages of the present disclosure, the preparation method of resveratrol nervonic acid ester is provided, comprising the following steps of:
step 1: weighing resveratrol, nervonic acid and thiocarbonyldiimidazole according to a molar ratio of 1:1:0.8 to 1:7:11.2 in a reactor;
step 2: adding a certain amount of solvent into the reactor to completely dissolve the reactants; and
step 3: stirring for reaction at room temperature for 30 min to 180 min.

It is preferable that the preparation method of resveratrol nervonic acid ester further comprises the following steps of:
step 4: separating and purifying the synthetic sample by using column chromatography, with the column being wet-packed with a 300-mesh silica gel as a stationary phase, and a petroleum ether and an ethyl acetate as a mobile phase in a volume ratio of 10:1 to 10:6; and
step 5: carrying out a rotary evaporation at 100 hPa to 130 hPa and 20° C. to 45° C., to obtain a pure product of resveratrol nervonic acid ester.

It is preferable that in the preparation method of resveratrol nervonic acid ester, resveratrol, nervonic acid and thiocarbonyldiimidazole are weighed according to a molar ratio of 1:6:9 in a reactor;

It is preferable that in the preparation method of resveratrol nervonic acid ester, the solvent is dichloromethane.

In the preparation method of resveratrol nervonic acid ester, it is preferable that in the step 2, the reactor is sealed to prevent the solvent from evaporating.

In the preparation method of resveratrol nervonic acid ester, it is preferable that in the step 3, the rotating speed of the stirring is 300 rpm to 800 rpm.

In the preparation method of resveratrol nervonic acid ester, it is preferable that in the step 3, the rotating speed of the stirring is 500 rpm and the reaction lasts for 60 min.

In the preparation method of resveratrol nervonic acid ester, it is preferable that in the step 4, the volume ratio of the petroleum ether to the ethyl acetate is 10:3, and in the step 5, the rotary evaporation is carried out at 100 hPa and 40° C.

The present disclosure includes at least the following beneficial effects:
(1) the highest esterification rate, yield and purity of the synthesized resveratrol nervonic acid ester can reach up to 99.61%, 80.68% and 91.66%, which are far higher than those of the existing methods;
(2) the one-step method catalyzed by thiocarbonyldiimidazole can rapidly synthesize resveratrol neurates in half an hour at the earliest at room temperature, and no toxic and harmful substances are produced in the synthesis process, and the whole synthesis process is mild, simple, green and pollution-free;
(3) compared with resveratrol, the esterified resveratrol nervonic acid ester has a significant increase in lipid solubility (increased by 61.2 to 204.1 times) and thermal stability (increased by 10° C.); and
(4) resveratrol nervonic acid ester has an enhanced oxidation resistance, and can be applied to inhibit the oxidation of oil and fats and prolong the shelf life of edible oils.

Other advantages, objectives, and features of the present disclosure will be embodied in part, by the following description and, in part, will also be understood by those skilled in the art through the study and practice of the present disclosure.

DESCRIPTION OF THE EMBODIMENTS

Figure 1:
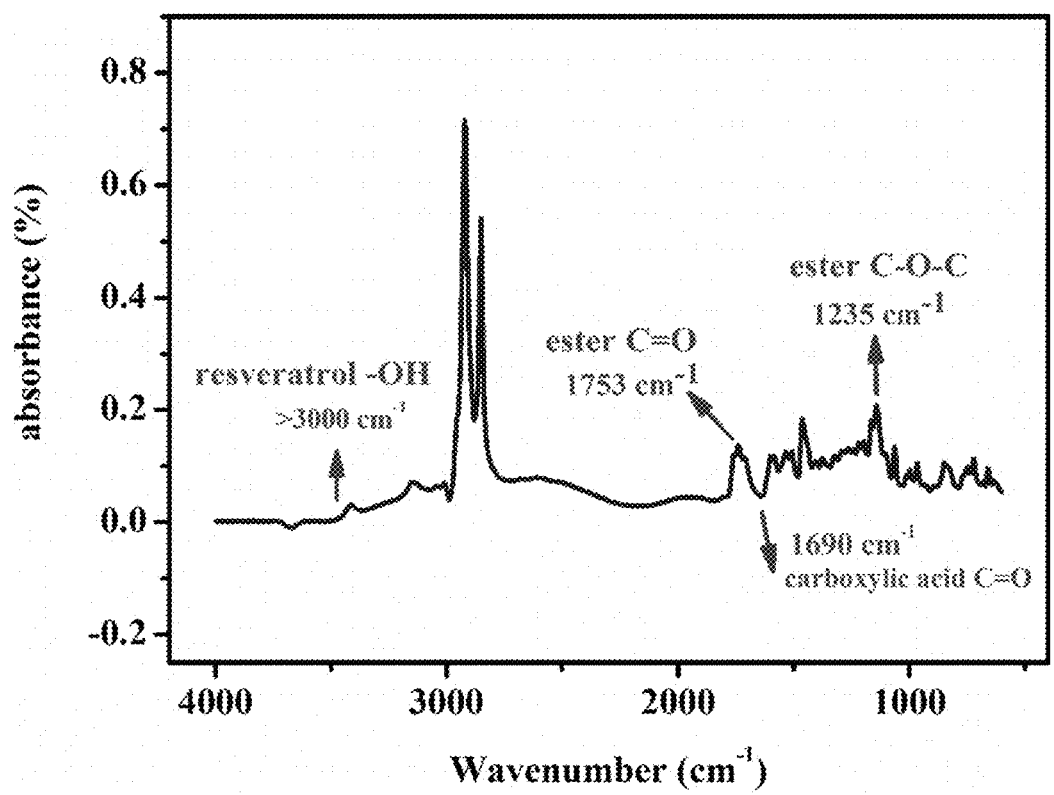
FIG. 1 is an infrared spectrogram of resveratrol nervonic acid ester according to one embodiment of the present disclosure.

The present disclosure will be further described in detail below in conjunction with the accompanying drawings and embodiments, so that those skilled in the art can implement the present disclosure with reference to the text of the specification.

It should be noted that the experimental methods described in the following embodiments are all conventional unless otherwise specified, and the reagents and materials described are commercially available unless otherwise specified.

1. One-Step Synthesis of Resveratrol Nervonic Acid Ester

Experiments were carried out at different molar ratios of resveratrol to nervonic acid molar ratios from A1 to A5 (1:1, 1:2, 1:3, 1:6, 1:7), and molar ratios of nervonic acid to thiocarbonyldiimidazole from B1 to B5 (1:0.8, 1:1, 1:1.2, 1:1.5, 1:1.6), as well as at different esterification times of C1-C5 (0.5 h, 1 h, 2 h, 3 h, 4 h), solvent amounts of D1-D5 (5 mL, 10 mL, 15 mL, 20 mL, 25 mL), and esterification temperatures of E1 and E2 (0° C., 25° C.). When determining the optimal parameters, the other parameters such as the amount of resveratrol, the molar ratio of resveratrol to nervonic acid, the molar ratio of nervonic acid to thiocarbonyldiimidazole, the esterification time, the solvent amount and the esterification temperature were controlled at 0.31 g, 1:3, 1:1, 0.5 h, 5 mL and 25° C., respectively.

As can be seen from Table 1, the esterification rates of resveratrol nervonic acid ester at different ratios of resveratrol to nervonic acid are all above 95%, and the highest esterification rate is 97.87% when the molar ratio of resveratrol to nervonic acid is 1:6. This may be due to the fact that the excessive addition of nervonic acid contributes to complete esterification, but after a certain percentage, the esterification is complete and the esterification rate no longer increases. The esterification rates of resveratrol nervonic acid ester at different ratios of nervonic acid to thiocarbonyldiimidazole are all above 90%, and the highest esterification rate is 95.21% when the molar ratio of nervonic acid to hiocarbonyldiimidazole is 1:1.5. As a condensing agent, thiocarbonyldiimidazole (TCDI), like the nervonic acid, contributes to the esterification reaction in an appropriate excess. The esterification rates of resveratrol nervonic acid ester with different esterification modification time are above 90%, and the highest esterification rate is 92.70% when the esterification modification lasts for 1 h. This may be because the esterification rate increases with the increase of the esterification time and then is affected by other factors and no longer increases. The esterification rates of resveratrol nervonic acid ester with different solvent addition amounts are above 80%, and the highest esterification rate is 91.94% when the solvent addition amount is 5 mL. Due to the fact that the experiment has to be reacted in a solvent and the amount of solvent added cannot be smaller, the optimal amount of solvent added is determined to be 5 mL. The esterification rates of resveratrol nervonic acid ester with different temperatures are all above 91%, and the esterification rate is higher at room temperature of 25° C. It may be that a low temperature is not conducive to the activation of carboxyl groups by thiocarbonyldiimidazole, while a too high temperature may lead to the volatilization of dichloromethane.

In summary, the optimal parameters for synthesis of a crude resveratrol nervonic acid ester sample are determined, that is, the resveratrol (M=228.24) (0.31 g, 0.001358 mol), nervonic acid (M=366.6) (3 g, 0.00818 mol) and thiocarbonyldiimidazole (M=178.21) (2.19 g, 0.0127 mol) were weighed in a molar ratio of 1:6:9 into an Erlenmeyer flask, then 5 mL of dichloromethane (0.0937 mol) was added to completely dissolve, with the opening being sealed with plastic wrap to prevent the solvent from volatilizing. The reaction with magnetic stirring (rotating speed of 500 rpm) was carried out at 25° C. and lasted for 1 h, and a crude sample of resveratrol nervonic acid ester with the esterification rate of 99.61% could be obtained by synthesizing.

TABLE 1

Experimental results of esterification rate of resveratrol nervonic acid ester synthesized at different parameters.

| No. | Molar ratio of resveratrol to nervonic acid | Esterification rate (%) |
| --- | --- | --- |
| A1 | 1:1 | 96.82 ± 0.42 |
| A2 | 1:2 | 96.96 ± 0.90 |
| A3 | 1:3 | 95.29 ± 1.32 |
| A4 | 1:6 | 97.87 ± 2.03 |
| A5 | 1:7 | 96.37 ± 1.33 |

| | Molar ratio of nervonic acid to thiocarbonyldiimidazole | Esterification rate (%) |
| --- | --- | --- |
| B1 | 1:0.8 | 91.61 ± 0.79 |
| B2 | 1:1 | 92.86 ± 1.76 |
| B3 | 1:1.2 | 94.01 ± 1.12 |
| B4 | 1:1.5 | 95.21 ± 1.40 |
| B5 | 1:1.6 | 95.01 ± 0.05 |

| | Esterification time (h) | Esterification rate (%) |
| --- | --- | --- |
| C1 | 0.5 | 91.82 ± 1.24 |
| C2 | 1 | 92.70 ± 1.43 |
| C3 | 2 | 90.96 ± 1.32 |
| C4 | 3 | 91.01 ± 0.21 |
| C5 | 4 | 91.06 ± 0.32 |

TABLE 1-continued

Experimental results of esterification rate of resveratrol nervonic acid ester synthesized at different parameters.

| | Amount of solvent added (mL) | Esterification rate (%) |
|---|---|---|
| D1 | 5 | 91.94 ± 4.80 |
| D2 | 10 | 90.22 ± 2.59 |
| D3 | 15 | 85.38 ± 1.59 |
| D4 | 20 | 81.24 ± 3.26 |
| D5 | 25 | 81.75 ± 4.60 |

| | Esterification temperature (° C.) | Esterification rate (%) |
|---|---|---|
| E1 | 0 | 91.28 ± 2.84 |
| E2 | 25 | 91.93 ± 1.50 |

The synthesized crude sample was further separated and purified by using column chromatography, wherein a 300-mesh silica gel was used as a stationary phase, a petroleum ether and an ethyl acetate in a ratio of 10:1 to 10:6 (v/v) was used as a mobile phase (eluent), the ratio of the petroleum ether to the ethyl acetate was preferably 10:3 (v/v), which could separate different types of esterified products, the ratio of the stationary phase to the mobile phase was 1: (v/v), and the column was wet-packed. The mobile phase, solvent and other impurities in the crude sample were removed by using a rotary evaporator at a pressure between 100 hPa and 130 hPa and a temperature between 20° C. and 45° C., and a pure product of resveratrol nervonic acid ester was obtained. It is preferable that the pressure was 100 hPa and the temperature was 40° C. After redissolution and volatilization, the pure product was weighed, and the yield was determined by calculating. Under optimal conditions, the pure product of resveratrol nervonic acid ester has achieved the highest yield of 80.68% and the highest purity of 91.66%.

Optimal Example 1

Resveratrol (M=228.24) (0.31 g, 0.001358 mol), nervonic acid (M=366.6) (3 g, 0.00818 mol) and thiocarbonyldiimidazole (M=178.21) (2.19 g, 0.0127 mol) in a molar ratio of 1:6:9 were weighed into an Erlenmeyer flask, then 5 mL of dichloromethane (0.0937 mol) was added to completely dissolve, with the opening being sealed with plastic wrap to prevent the solvent from volatilizing. Followed by a reaction at 25° C. for 1 h under magnetic stirring (rotating speed of 500 rpm), a crude sample of resveratrol nervonic acid ester was obtained via synthesizing. A column chromatography was used for separation and purification, with a ratio of petroleum ether to ethyl acetate being 10:3 (v/v) as a mobile phase. The mobile phase, solvent and other impurities in the crude sample were then removed in a rotary evaporation at a pressure of 100 hPa and a temperature of 40° C. to obtain the pure product of resveratrol nervonic acid ester.

Embodiment 2

Resveratrol (M=228.24) (0.31 g, 0.001358 mol), nervonic acid (M=366.6) (3 g, 0.00818 mol) and thiocarbonyldiimidazole (M=178.21) (2.19 g, 0.0127 mol) in a molar ratio of 1:6:9 were weighed into an Erlenmeyer flask, then 5 mL of dichloromethane (0.0937 mol) was added to completely dissolve, with the opening being sealed with plastic wrap to prevent the solvent from volatilizing. Followed by a reaction at 25° C. for 1 h under magnetic stirring (rotating speed of 300 rpm), a crude sample of resveratrol nervonic acid ester was obtained via synthesizing. A column chromatography was used for separation and purification, with a ratio of petroleum ether to ethyl acetate being 10:3 (v/v) as a mobile phase. The mobile phase, solvent and other impurities in the crude sample were then removed in a rotary evaporation at a pressure of 100 hPa and a temperature of 40° C. to obtain the pure product of resveratrol nervonic acid ester.

Comparative Example 1

Resveratrol (M=228.24) (0.31 g, 0.001358 mol), nervonic acid (M=366.6) (3 g, 0.00818 mol) and thiocarbonyldiimidazole (M=178.21) (2.19 g, 0.0127 mol) in a molar ratio of 1:6:9 were weighed into an Erlenmeyer flask, then 5 mL of dichloromethane (0.0937 mol) was added to completely dissolve, with the opening being sealed with plastic wrap to prevent the solvent from volatilizing. Followed by a reaction at 25° C. for 1 h under magnetic stirring (rotating speed of 500 rpm), a crude sample of resveratrol nervonic acid ester was obtained via synthesizing. A column chromatography was used for separation and purification, with a volume ratio of petroleum ether to ethyl acetate being 10:6 (v/v) as a mobile phase. The mobile phase, solvent and other impurities in the crude sample were then removed in a rotary evaporation at a pressure of 100 hPa and a temperature of 40° C. to obtain the pure product of resveratrol nervonic acid ester.

Comparative Example 2

Resveratrol (M=228.24) (0.31 g, 0.001358 mol), nervonic acid (M=366.6) (3 g, 0.00818 mol) and thiocarbonyldiimidazole (M=178.21) (2.19 g, 0.0127 mol) in a molar ratio of 1:6:9 were weighed in an Erlenmeyer flask, then 5 mL of dichloromethane (0.0937 mol) was added to completely dissolve, with the opening being sealed with plastic wrap to prevent the solvent from volatilizing. Followed by a reaction at 25° C. for 1 h under magnetic stirring (rotating speed of 500 rpm), a crude sample of resveratrol nervonic acid ester was obtained via synthesizing. A column chromatography was used for separation and purification, with a volume ratio of petroleum ether to ethyl acetate being 10:3 (v/v) as a mobile phase. The mobile phase, solvent and other impurities in the crude sample were then removed in a rotary evaporation at a pressure of 80 hPa and a temperature of 40° C. to obtain the pure product of resveratrol nervonic acid ester.

Comparative Example 3

Resveratrol (M=228.24) (0.31 g, 0.001358 mol), nervonic acid (M=366.6) (3 g, 0.00818 mol) and thiocarbonyldiimidazole (M=178.21) (2.19 g, 0.0127 mol) in a molar ratio of 1:6:9 were weighed into an Erlenmeyer flask, then 5 mL of dichloromethane (0.0937 mol) was added to completely dissolve, with the opening being sealed with plastic wrap to prevent the solvent from volatilizing. Followed by a reaction at 25° C. for 1 h under magnetic stirring (rotating speed of 500 rpm), wa obtained via synthesizing. A column chromatography was used for separation and purification, with a volume ratio of petroleum ether to ethyl acetate being 10:3 (v/v) as a mobile phase. The mobile phase, solvent and other impurities in the crude sample were then removed in a rotary evaporation at a pressure of 100 hPa and a temperature of 25° C. to obtain the pure product of resveratrol nervonic acid ester.

Comparative Example 4

Resveratrol (M=228.24) (0.31 g, 0.001358 mol), conjugated linoleic acid (M=280.4) (2.29 g, 0.00818 mol) and thiocarbonyldiimidazole (M=178.21) (2.19 g, 0.0127 mol) in a molar ratio of 1:6:9 were weighed into Erlenmeyer flasks, then 5 mL of dichloromethane (0.0937 mol) was added to completely dissolve, with the opening being sealed with plastic wrap to prevent the solvent from volatilizing. Followed by a reaction at 25° C. for 1 h under magnetic stirring (rotating speed of 500 rpm), a crude sample of resveratrol conjugated linoleate was synthesized. A column chromatography was used for separation and purification, with a ratio of petroleum ether to ethyl acetate being 10:3 (v/v) as a mobile phase. The mobile phase, solvent and other impurities in the crude sample were then removed in a rotary evaporation at a pressure of 100 hPa and a temperature of 40° C. to obtain the pure product of resveratrol conjugated linoleate.

Comparative Example 5

Resveratrol conjugated linoleate was prepared according to the most preferable method of Patent No. ZL 202011585264.X.

The esterification rates, purity and yield of the samples under Embodiments 1 and 2 and Comparative Examples 1 to 5 are shown in Table 2.

TABLE 2

Esterification rates, purities and yields of samples under Embodiments and Comparative Examples

|  | Esterification rate (%) | Purity (%) | Yield (%) |
| --- | --- | --- | --- |
| Embodiment 1 | 99.61 | 91.66 | 80.68 |
| Embodiment 2 | 96.01 | 89.03 | 77.39 |
| Comparative Example 1 | 50.35 | 85.28 | 47.28 |
| Comparative Example 2 | 78.46 | 87.05 | 71.43 |
| Comparative Example 3 | 77.26 | 68.40 | 70.22 |
| Comparative Example 4 | 97.51 | 98.52 | 60.22 |
| Comparative Example 5 | 96.87 | 98.00 | 60.00 |

2. Determination of Ester Production by Infrared Spectroscopy 500 mg of the sample prepared in Embodiment 1 was weighed onto an infrared spectral bath, and the infrared absorption spectrum was immediately collected with air as the background. 64 scans were performed at a resolution of 16 $cm^{-1}$, and a spectrum in a range of 500 $cm^{-1}$ to 4500 $cm^{-1}$ was recorded at a resolution of 4 $cm^{-1}$ (FIG. 1), from which the production of the resveratrol nervonic acid ester was determined based on its absorption peak. After the detection of resveratrol neuronate produced in Embodiment 1, the C=O peak of the carboxylic acid group of neuronic acid was obviously reduced (1690 $cm^{-1}$), the ester C=O group peak was obviously produced (1753 $cm^{-1}$), and no obvious strong peak, namely the peak of the hydroxyl O—H group of resveratrol (3187 $cm^{-1}$), was observed above 3000 $cm^{-1}$. All three hydroxyl groups of resveratrol were reacted to generate the resveratrol nervonic acid ester product.

3. Determination of Esterification Rate 0.5 g of the sample was taken, 2 mL of ethanol with a volume fraction of 80% was added to extract resveratrol, and then the supernatant was taken prior to repeating the extraction step and collected to level to 5 mL. An ultra-high-phase liquid chromatography was used to detect the content of resveratrol. In some samples, the remaining amount of resveratrol was high, and so an ethanol with a volume fraction of 80% could be used for detection after multiple dilutions. The liquid chromatography was carried out under following conditions: the chromatographic column model was C18 (2.1 mm×100 mm, 1.8 μm), the column temperature was 35° C., the detection wavelength was 285 nm/306 nm, the injection volume was 10 μL, and the mobile phases A and B were 0.1% aqueous formic acid and pure methanol at a flow rate of 0.45 mL/min. Gradient elution was carried out with a 90% A phase at 0 min to 0.5 min, a 75% A phase at 2 min, a 70% A phase at 3.5 min, a 65% A phase at 4 min, a 50% A phase at 5 min, a 10% A phase at 7 min, and a 90% A phase at 7.2 min to 10 min.

4. Determination of Purity 0.2 g of sample was weighed into a 10 mL plastic centrifuge tube, and 2.0 mL of C18:0 internal standard solution was added followed by the addition of 100 μL of 2 mol/L potassium hydroxide methanol solution. A vortex oscillation was carried out for 30 s until the sample solution was well mixed, flowed by a centrifugation for 10 min at 4000 rpm. 20 μL of the supernatant was then pipetted, added into a volumetric flask with 1 mL constant volume of chromatographic grade isooctane, and placed at room temperature for detecting. The injection parameters were selected as follows: the split ratio was set at 60:1; the linear speed was set at 9.0 cm/s; the injection volume was set at 1 μL; the inlet temperature was set at 230° C.; and the chromatographic column flow rate was set at 0.6 mL/min. The heating program were selected as follows: for SLB-IL111 capillary chromatographic column, the initial temperature was set at 60° C.; after being kept for 5 min, the temperature was warmed up to 175° C. at a rate of 20° C./min; after being continued to be kept for 15 min, the temperature was warmed up to 185° C. at a rate of 1° C./min; and finally the temperature was kept for 70 min. Detection parameters were as follows: hydrogen flame was used for the detector; the temperature of the detector was set at 250° C.; the tail blowing flow rate of air was set at 30.0 mL/min; the hydrogen flow rate was 40 mL/min; the air flow rate was 400 mL/min; the carrier gas was high purity nitrogen; the pressure of the inlet was 192.2 kPa, with total flow rate of 31.5 mL/min; and the purge flow rate was 1.0 mL/min.

5. Detection of Thermal Stability

Figure 2:
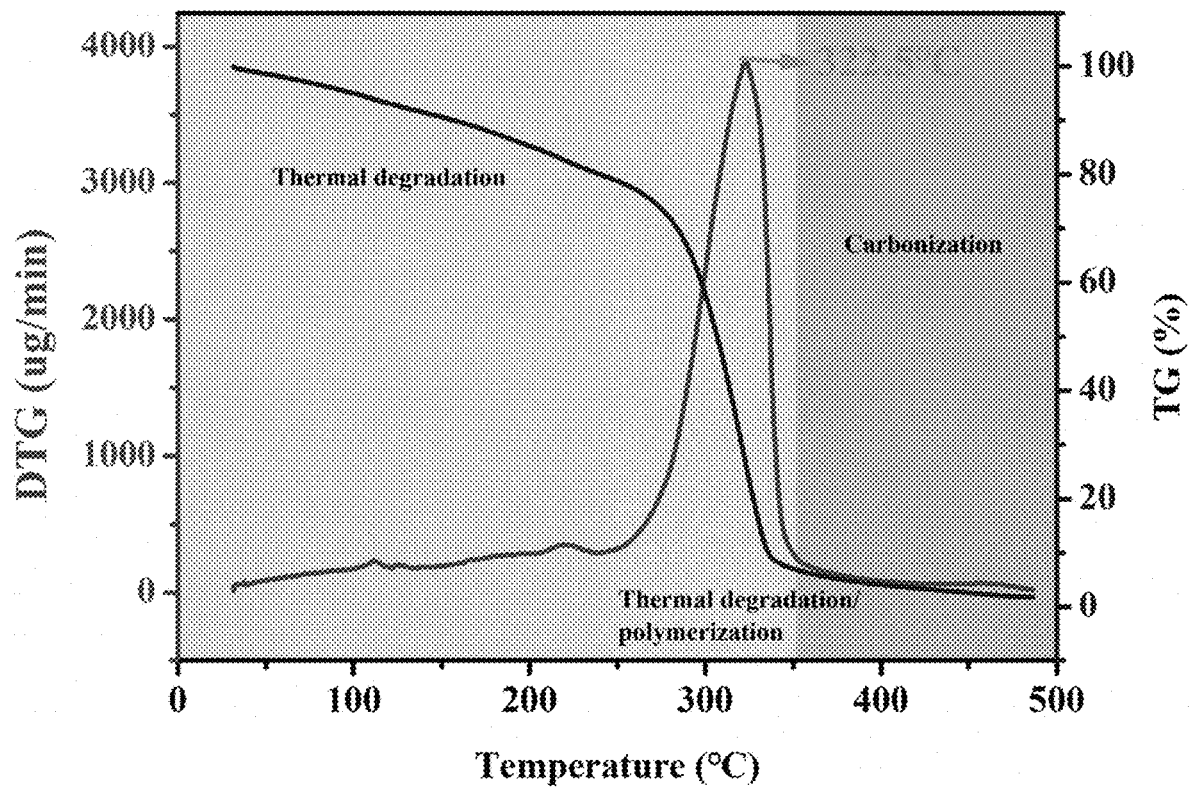
FIG. 2 is a thermogravimetric diagram of resveratrol nervonic acid ester according to one embodiment of the present disclosure.

An appropriate amount of pure product of Embodiment 1 (about 50 mg) was weighed into a small aluminium box, and the weight of the sample was recorded after equilibration. For a thermogravimetric equipment, the temperature was selected to be 0° C. to 500° C., the heating rate to be 20° C./min, and the nitrogen flow rate to be 100 mL/min, and a thermogravimetric change curve was recorded. The initial reaction temperature was 300° C. according to a baseline extrapolation method. Compared with resveratrol (290° C.), the thermal stability temperature of resveratrol nervonic acid ester sample was increased by 10° C. Curves A and B in FIG. 2 represent the rate of mass change and the mass change with increasing temperature, respectively.

6. Detection of Lipid Solubility

An appropriate amount of pure product of Embodiment 1 was accurately weighed into a 100 mL triangular flask, and after heating to 60° C. in a water bath, a peanut oil was added drop-wise into the triangular bottle and kept stirring until the resveratrol nervonic acid ester were completely dissolved by the peanut oil and the system exhibits a homogeneous phase. After being cooled to 20° C. and left to stand for 24 h, an observation to the triangular flask for precipitation or turbidity was performed, and the solubility was calculated based on the amount of peanut oil added. After the experiment, the lipid solubility of resveratrol was 0.98 μg/g, and the lipid solubility of resveratrol nervonic acid ester of Embodiment 1 was 60 μg/g to 200 μg/g, which was increased by 61.2 times to 204.1 times as compared with that of resveratrol, and the lipid solubility of resveratrol conjugated linoleate of Comparative Examples 4 and 5 were increased by 20 times to 21 times as compared with that of resveratrol.

7. Detection of Oxidation Stability

Resveratrol as well as the pure products (10 mg) of Embodiment 1, Embodiments 4 and 5 were dissolved in an 80% methanol solution (1 mL), respectively, and the supernatants were obtained by vortexing and uniformly mixing, and centrifuging at 4000 rpm for 10 min. 400 μL of supernatant was mixed with 600 μL of 80% methanol solution or DPPH working solution to synthesize a control tube and a test tube respectively, and blank tubes were 400 μL of methanol solution and 600 μL of DPPH working solution. After mixing uniformly, the tubes were left to stand at room temperature in dark for 30 min, and the supernatants were collected after being centrifuged at 4000 rpm for 5 min. The absorbance values of the tubes were measured at a wavelength of 517 nm with anhydrous ethanol as the background, and all measurements were repeated for three times. The antioxidant activity was calculated according to the following equation (1):

DPPH radical scavenging activity (%)=100×(1−(A test tube−A control tube)/A blank tube)  (1)

According to the experimental results, the antioxidant activity of resveratrol and resveratrol conjugated linoleate of Comparative Examples 4 and 5 were 87.49% and 88.10-88.28%, respectively, while the antioxidant activity of resveratrol nervonic acid ester of Embodiment 1 was 90.00%, which was 1.03 and 1.01 times higher than that of resveratrol and resveratrol conjugated linoleate, respectively.

Figure 3:
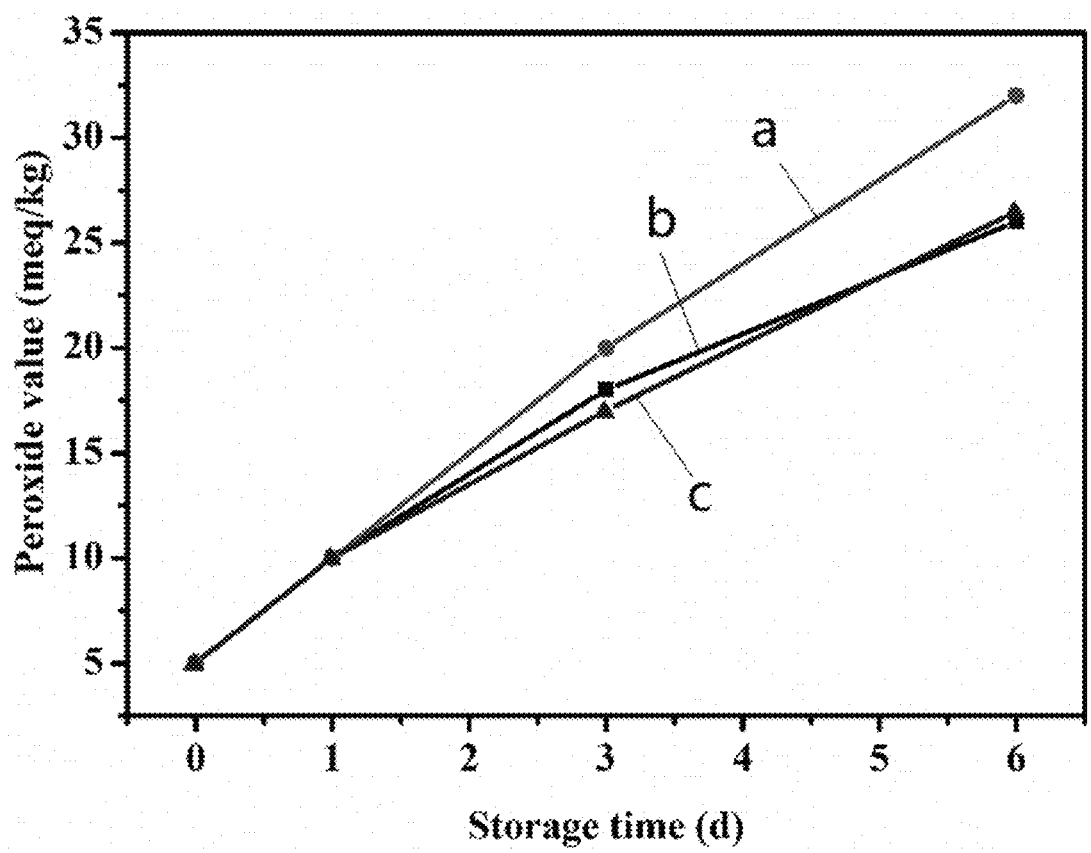
FIG. 3 is a peroxide value detection diagram of resveratrol nervonic acid ester according to one embodiment of the present disclosure.
Figure 4:
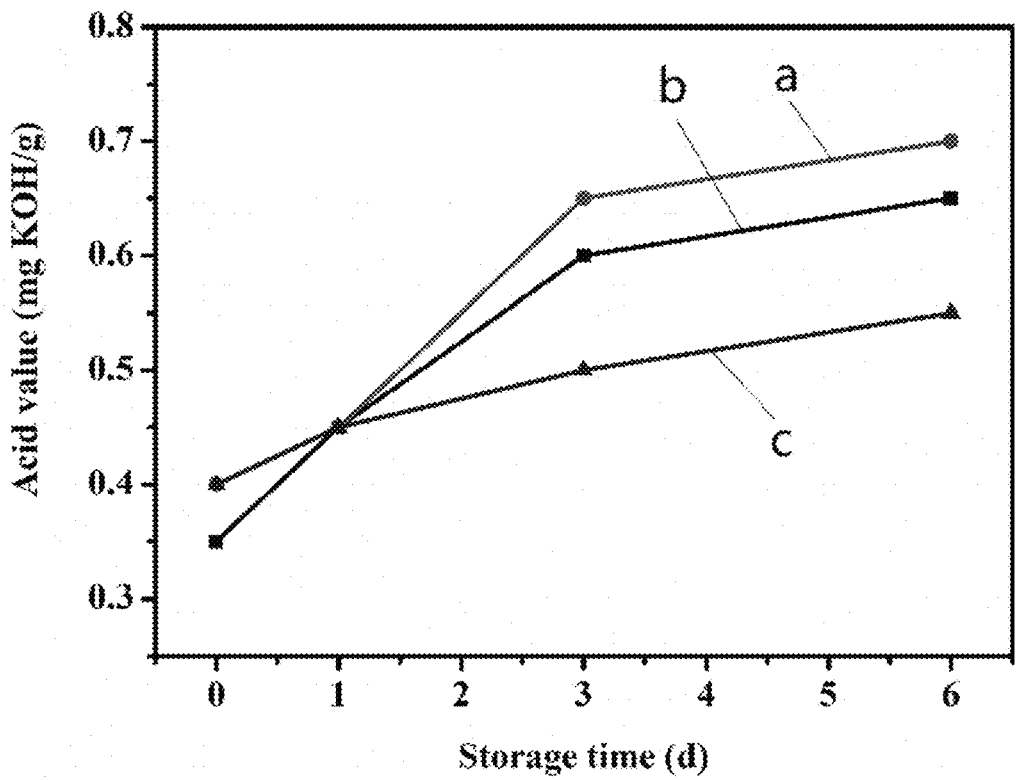
FIG. 4 is an acid value detection diagram of resveratrol nervonic acid ester according to one embodiment of the present disclosure.
Figure 5:
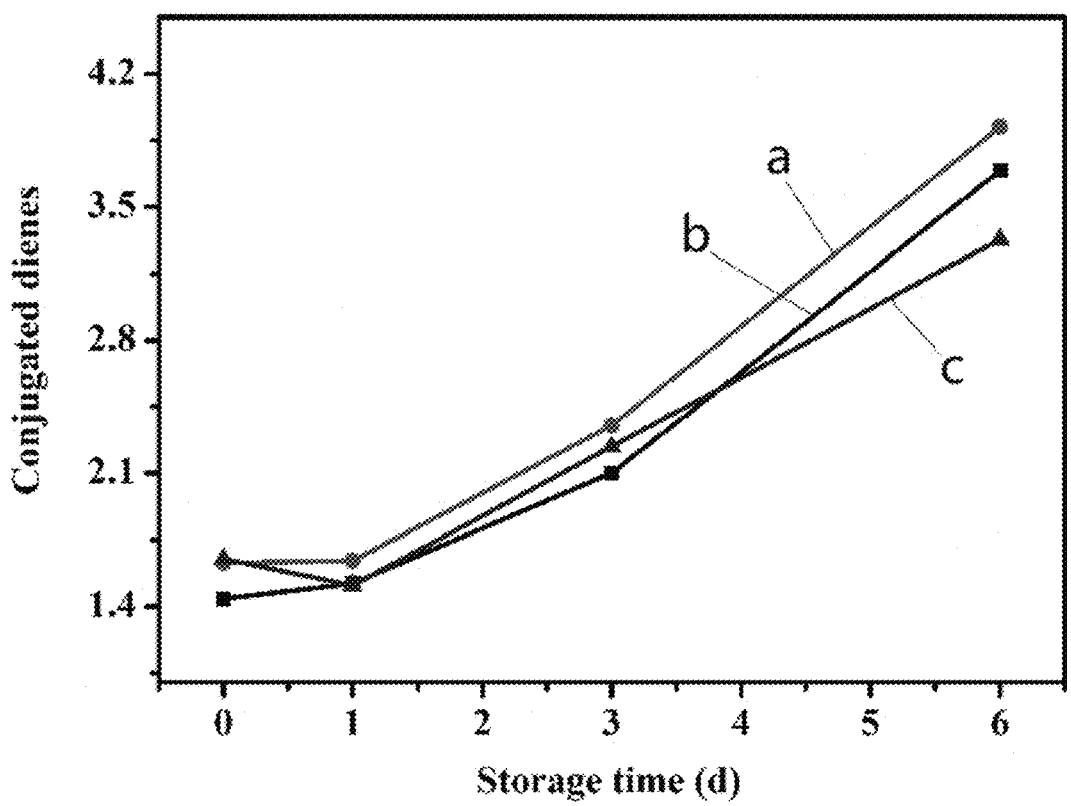
FIG. 5 is a conjugated diene value detection diagram of resveratrol nervonic acid ester according to one embodiment of the present disclosure.

Five parts of 25 g of corn oil with endogenous antioxidant removed were weighed and added into 10 mL flasks respectively, two of which were added with 5 mg of pure product in Embodiment 1 and resveratrol respectively, and the other two parts were added with 5 mg of pure products in Comparative Examples 4 and 5 respectively, with a concentration of 200 ppm and in addition, one another part was prepared and used as a blank control (no antioxidant added). After blow-drying the ethanol solution with nitrogen, the flasks were wrapped with aluminum foil to prevent light exposure. The flasks were placed in an oven at 60±0.5° C. After 0, 1, 3, and 6 days, samples were collected, the acid value, peroxide value, and conjugated diene value thereof were detected, and the shelf lives were detected. The acid value and peroxide value were detected by an acid value peroxide value detector. About 0.1 g (exactly 0.0001 g) of the oil sample was weighed into a 25 mL volumetric flask, and dissolved and diluted to 25 mL with isooctane. The absorbance was measured at 232 nm using a spectrophotometer with isooctane solvent as blank. The shelf life of edible oil was measured by using an oil oxidation induction instrument to detect the oxidation induction time at different temperatures (100° C., 110° C., 120° C. and 130° C.), and the shelf life (oxidation induction time at 20° C.) were calculated based on the derivatives of the induction time. As can be seen from the results, the peroxide value (FIG. 3), acid value (FIG. 4) and conjugated diene value (FIG. 5) of resveratrol nervonic acid ester were basically lower than those of resveratrol and blank control. Curves a, b and c in FIG. 3 to FIG. 5 correspond to the blank group, resveratrol and pure product of Embodiment 1, respectively. The peroxide value, acid value, conjugated diene value, and shelf life of Embodiment 1, Comparative Example 4, Comparative Example 5, resveratrol and blank group after 6 days are shown in Table 3.

TABLE 3

Peroxide value, acid value and conjugated diene value, and shelf life test results

| | Peroxide value (meq/kg) | Acid value (mgKOH/g) | Conjugated diene value | Shelf life (day) |
|---|---|---|---|---|
| Pure product of Embodiment 1 | 26.5 | 0.55 | 3.33 | 78.2 |
| Pure product of Comparative Example 4 | 27 | 0.60 | 3.60 | 71.4 |
| Pure product of Comparative Example 5 | 27.5 | 0.60 | 3.65 | 71.3 |
| Resveratrol | 26 | 0.65 | 3.69 | 68.5 |
| Blank control | 32 | 0.7 | 3.92 | 31.9 |

Despite the embodiments disclosed above, the present disclosure is not limited to the applications listed in the specification and the embodiments. The present disclosure can be fully applied to various fields suitable for thereof, and additional modifications can be readily made by those skilled in the art. Therefore, without departing from the general concepts defined by the appended claims and equivalents, the present disclosure is not limited to the specific details and diagrams shown and described herein.

What is claimed is:

1. A preparation method of resveratrol nervonic acid ester, comprising the following steps of:
    step 1: weighing resveratrol, a nervonic acid and thiocarbonyldiimidazole according to a molar ratio of 1:6:9 in a reactor;
    step 2: adding a certain amount of solvent into the reactor to completely dissolve a reactants; and
    step 3: stirring for reaction at room temperature for 30 min to 180 min.

2. The preparation method of resveratrol nervonic acid ester according to claim 1, further comprising the steps of:
    step 4: separating and purifying the synthetic sample by using column chromatography, with the column being wet-packed with a 300-mesh silica gel as a stationary phase, and a petroleum ether and an ethyl acetate as a mobile phase in a volume ratio of 10:1 to 10:6; and
    step 5: carrying out rotary evaporation at 100 hPa to 130 hPa and 20° C. to 45° C. to obtain a pure product of resveratrol nervonic acid ester.

3. The preparation method of resveratrol nervonic acid ester according to claim 1, wherein the solvent is dichloromethane.

4. The preparation method of resveratrol nervonic acid ester according to claim 1, wherein in the step 2, the reactor is sealed to prevent the solvent from evaporating.

5. The preparation method of resveratrol nervonic acid ester according to claim 1, wherein in the step 3, the stirring is carried out at a rotating speed of 300 rpm to 800 rpm.

6. The preparation method of resveratrol nervonic acid ester according to claim 5, wherein in the step 3, the stirring is carried out at the rotating speed of 500 rpm and the reaction lasts for 60 min.

7. The preparation method of resveratrol nervonic acid ester according to claim 2, wherein in the step 4, the volume ratio of the petroleum ether to the ethyl acetate is 10:3, and in the step 5, the rotary evaporation is carried out at 100 hPa and 40° C.

\* \* \* \* \*